United States Patent [19]
Malchesky et al.

[11] Patent Number: 5,516,648
[45] Date of Patent: May 14, 1996

[54] ENCAPSULATED BIOLOGICAL INDICATOR

[75] Inventors: Paul S. Malchesky, Painesville Township; Donna M. Richardson, Parma, both of Ohio

[73] Assignee: Steris Corporation, Mentor, Ohio

[21] Appl. No.: 292,737

[22] Filed: Aug. 18, 1994

[51] Int. Cl.$^6$ .............................. C12Q 1/02; C12Q 1/22; C12N 1/00

[52] U.S. Cl. .................. 435/31; 435/4; 435/29; 435/32; 435/174; 435/176; 435/177; 435/180; 435/182; 435/832

[58] Field of Search ................... 435/174, 176, 435/177, 180, 182, 4, 29, 31, 32, 832, 296

[56] References Cited

U.S. PATENT DOCUMENTS

| | | | |
|---|---|---|---|
| 4,461,837 | 7/1984 | Karle et al. | 435/296 |
| 4,743,537 | 5/1988 | McCormick et al. | 435/296 |
| 4,885,253 | 12/1989 | Kralovic | 435/296 |
| 4,918,003 | 4/1990 | Macaro et al. | 435/31 |
| 4,937,115 | 6/1990 | Leatherman | 428/36.4 |

FOREIGN PATENT DOCUMENTS

| | | |
|---|---|---|
| 342783A2 | 11/1989 | European Pat. Off. . |
| 3705596A1 | 9/1988 | Germany . |
| WO95/06134 | 3/1995 | WIPO . |
| WO95/21936 | 8/1995 | WIPO . |

OTHER PUBLICATIONS

"Porex® Porous Plastics High Performance Materials" Porex Technologies Advertising Brochure (undated).

*Primary Examiner*—Donald E. Czaja
*Assistant Examiner*—Jane Williams
*Attorney, Agent, or Firm*—Fay, Sharpe, Beall, Fagan, Minnich & McKee

[57] ABSTRACT

Reference microorganisms are sealed into an interior cavity of a microporous membrane (14, 20). In one embodiment, the reference microbes are inoculated on a element (12) which is sealed in a microporous envelope (14) (FIG. 1). In another embodiment, the reference microbes (22) are loaded into an interior bore or cavity of a microporous plastic tube or envelope (20) (FIG. 3). The microporous membrane and the reference microbes, such as spores, are immersed concurrently with items to be microbially decontaminated separately into an anti-microbial fluid. The microporous membrane is constructed of a material which is sufficiently resistant to temperature, water, strong oxidants, and other anti-microbial agents or processes used for microbial decontamination or sterilization that it retains its integrity during the immersion in any common steam, gas, or liquid microbial decontamination or sterilization fluid or system. The micropores are sufficiently small that the reference microbes are entrapped, yet sufficiently open that anti-microbial steam, gas, or liquid are passed into the interior for direct contact with the reference microbes. After the microbial decontamination process, the microporous membrane and the contained reference microbes are immersed in a culture medium (40) and monitored to determine whether any of the reference microbes remain alive and commence growing.

7 Claims, 1 Drawing Sheet

5,516,648

ENCAPSULATED BIOLOGICAL INDICATOR

BACKGROUND OF THE INVENTION

The present invention relates to the art of biological indicators. It finds particular application in conjunction with spore inoculated elements used for indicating the completeness of a sterilization process and will be described with particular reference thereto.

Heretofore, various sterilization indicating systems have been provided. The systems generally included an element, e.g. a pad or strip, which was inoculated with a spore or other microorganism. In some systems, the pad was mounted in a container and connected with the container exterior by a tortuous path or otherwise. The container was disposed such that during a gas or high pressure steam sterilization process, the pad was subject to substantially the same sterilizing conditions by gas or high pressure steam that penetrates the tortuous path as the articles being sterilized. At the end of the sterilizing operation, the tortuous path was closed, a glass ampule containing a culture medium was fractured, and the pad and culture medium were brought together. After an appropriate incubation period, the culture medium was examined for evidence of growth of the inoculated microorganisms. A lack of microorganism growth was indicative of sterilization and growth of the microorganisms was indicative that the sterilization process was not complete. See, for example, U.S. Pat. Nos. 4,461,837 and 4,743,537.

A disadvantage of the prior art sterilization indicating systems was that the element containing the spores or other microorganisms was often times a spore strip pad. The spores, when contacted by sterilant or disinfectant mediums, could potentially be dislodged.

These problems have been addressed by placing the inoculated element in an envelope of sorts, the envelope being constructed from a semi-porous or non-porous material, and usually from paper. The paper, however, was easily dissolved when using a liquid sterilant or disinfectant or made it very difficult to transfer aseptically to culture medium, thus requiring that the strip be removed from the envelope prior to use, making it very difficult to transfer the strip aseptically to the culture medium. If the spore containing element or spore strip was removed from the envelope, however, the potential problem such as the spores being washed off of the strip may again be encountered.

The present invention provides a new and improved spore containing element which is suitable for use in steam, gas, or liquid sterilant systems, yet overcomes the above-referenced problems.

SUMMARY OF THE INVENTION

In accordance with one aspect of the present invention, an encapsulated biological indicator for gas, steam, or liquid chemical processors is provided. The spore strip or other spore-containing element of the indicator is encased or encapsulated in a microporous, hydrophilic membrane.

In accordance with another aspect of the present invention, an encapsulated biological indicator is provided which includes a microporous, hydrophilic membrane in the form of a sealed envelope into which has been deposited a spore strip or other spore containing element.

In accordance with a further aspect of the present invention, an encapsulated biological indicator is provided which includes a microporous, hydrophilic membrane in the form of an extruded tube. In this form, the spore strip or other spore-carrying element may be placed inside the tube, or the spores may be placed on the interior of the tube itself, without aid of a spore strip or other spore carrying element.

In accordance with yet another embodiment of the present invention, the encapsulated biological indicator which is the subject hereof is placed in a Universal Biological Indicator, such as that disclosed in U.S. Pat. No. 4,885,253, the disclosure of which is incorporated herein by reference. In this regard, the encapsulated biological indicator is used in place of the illustrated spore disk.

One advantage of the present invention is that the subject encapsulated biological indicator eliminates the potential for spores to be washed off of a spore strip or other spore carrying element.

Another advantage of the present invention is the elimination of the potential for operator contamination because the encapsulated biological indicator retains the spores in an inaccessible, interior cavity.

Yet another advantage of the present invention is that the encapsulated biological indicator is suitable for use with commercially available gas, steam, and liquid biological indicator systems.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
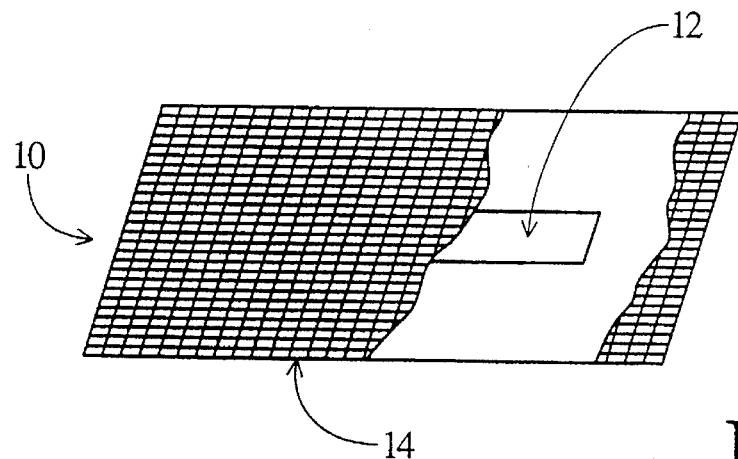
FIG. 1 is an illustration of a microorganism inoculated strip in a microporous membrane, particularly an envelope.

With reference to FIG. 1, a microorganism-inoculated, biological indicator 10 includes a spore inoculated element or strip 12. The spore inoculated element is wrapped or encapsulated in a microporous, hydrophilic membrane 14. The inoculated indicator element may be a spore strip, or any other suitable element inoculated with spores suitable for evaluating the completeness of a given sterilization system. Alternately, the spores may be charged directly to the interior region of the encapsulating membrane 14 without aid of any kind of carrying element such that the membrane carries the spores.

Typically, the microorganisms or spores are bacteria spores that have a resistance selected in accordance with the sterilizing, disinfecting, or other microbial decontamination procedure to be monitored. That is, microorganisms are selected which will be killed under more demanding decontamination conditions than bacteria or microorganisms typically on the items to be decontaminated. Further, the microorganisms are also selected to have a relatively fast growth rate or short reproduction time in a liquid culture medium. Various microbe inoculations and corresponding culture medium combinations are well-known in the art.

The microporous membrane encapsulant may be comprised of any suitable natural or synthetic copolymer material which is microporous in nature, and preferably which is hydrophilic. Exemplary of such materials are cellulosic membranes and organic polymer membranes including simple hydrocarbon membranes, such as polyethylene and polypropylene, as well as more polar structures, such as polyamide membranes which includes nylon, acrylic copolymers, polysulfone, polyethersulfone, ethylene vinyl alcohol, and polyacrylonitrile. The membrane encapsulant material is resistant to degradation by the liquid microbial decontamination solutions and remains porous. The encapsulant must also be resistant to strong oxidants such as peracetic acid, peroxides, hypochlorites, chlorine gas or ions, ethylene oxide gas, and the like, and be heat insensitive at higher or sterilization temperatures.

The membrane encapsulant material has micropores of a diameter slightly less than that of the spores contained within the interior region or cavity of the encapsulating membrane such that the spores cannot escape the interior of the membrane. Due to the porous nature of the encapsulating membrane, the decontamination medium, whether gas, steam, or liquid, easily flows to the interior of the membrane and contacts the spores or microorganisms. In this regard, it is important when using a liquid sterilant that the membrane be hydrophilic in nature so that the liquid sterilant solution wets the membrane and is transported through the pore structure of the membrane to the interior region or cavity thereof. Of course, if a membrane material is selected which is not normally hydrophilic in nature, the material may be treated in a manner known to those skilled in the art of using such materials to render the membrane hydrophilic.

The encapsulating membrane may be in the form of an envelope containing a spore strip or other inoculated element, such as a disk, of the kind known to those skilled in the art. In this instance, the membrane would be formed or produced and the inoculated element subsequently added to the membrane envelope. The term "envelope" as used herein includes any membrane configuration, such as pillows, tubes, and the like, which lends itself to the subsequent addition of a spore-inoculated element and which can then be sealed to retain the inoculated element therein.

Figure 2:
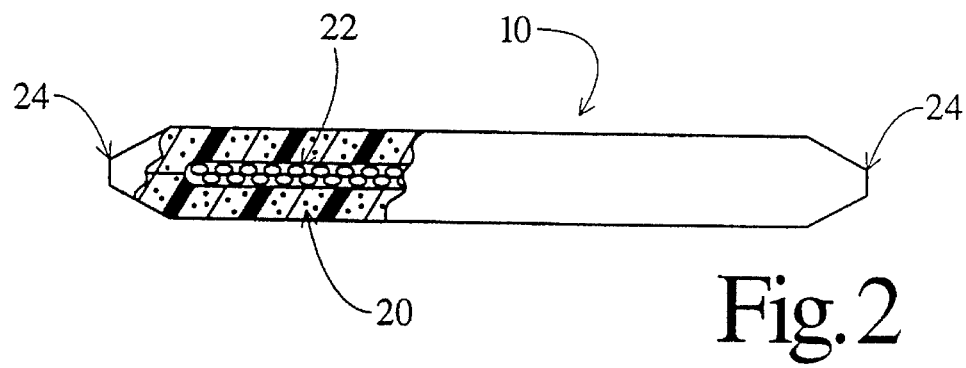
FIG. 2 is an alternate embodiment in which spores are extruded in an interior channel of microporous tubing; and, FIG. 3 illustrates a biological indicator system.

With reference to FIG. 2, the membrane may also be in the form of an extruded membrane tube 20 having spores 22 disposed in the interior thereof. In this type of indicator, the extrusion of the membrane and deposition or charging of spores to the interior of the membrane may be accomplished in a singular process. Conversely, the spores may be charged to the interior of the extruded membrane subsequent to extrusion. The extruded membrane containing the spores may then be sealed, for instance by heat sealing 24, to retain the spores therein. Exemplary of an extruded membrane would be a membrane in the form of a capillary tube of porous polyethylene, polypropylene, nylon, polysulfone, polyethersulfone, acrylic copolymers, ethylene vinyl alcohol, polyacrylonitrile, polycarbonate, polyphthalate carbonate, polytetrafluoroethylene, cellulosics, or the like.

The spores may be disposed in the membrane in a dry state, or may be disposed in the membrane in a suitable carrier medium. A suitable carrier medium will be any medium which does not interfere with or is non-reactive with the microbial decontaminant, which does not adversely affect or degrade the encapsulating membrane, and which is compatible with the culture media which the spores may eventually contact, e.g. it must not interfere with the growth of spores which may remain alive. In this latter case, interference with the culture media may result in a false negative, leading the user to believe incorrectly that the microbial decontamination system is functioning properly. Alternatively, the culture media may, upon contact with the membrane encapsulated spore-inoculated element, indicate viability of the spore sample by a color change of the media.

Figure 3:
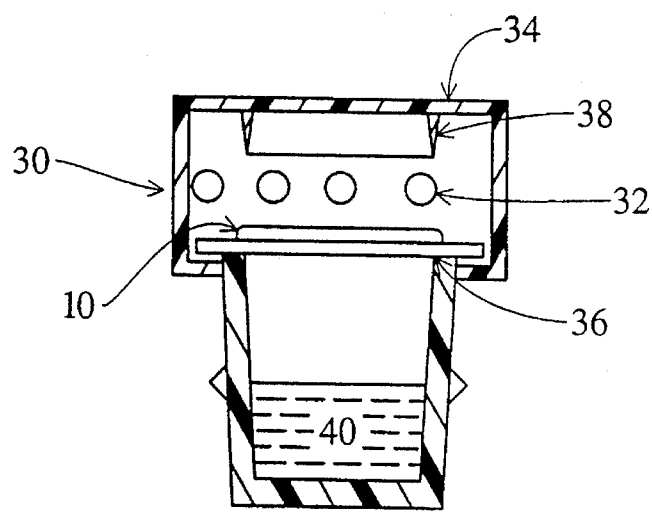

With reference to FIG. 3, it is contemplated that the present invention may be easily adapted for use in known biological indicator systems. For instance, in systems which employ a vial-type device 30, the subject encapsulated indicator 10 may be placed in a position such that it is in the flow path of the microbial decontaminant via apertures 32 in a cap 34. Apertures 32 may be large holes or slots, slits, or the like. After the decontamination cycle, the cap is depressed, or the cap may be screwed down, to sever a member 36 with a cutter 38 and release the encapsulated spore inoculated indicator 10 into a culture media 40, which may be a self-contained media vial. The cap in the depressed or closed position seals the culture media from the environment. Alternately, the spore strip can be transferred to a remote culture media container. In either instance, because any living spores are held within the encapsulating membrane 14, 20, there is no chance for contamination of the spores during transition to the culture media. A biological indicator system of the type which directly deposits the spore-carrying element into the culture media is taught and illustrated in U.S. Pat. No. 4,885,253. The subject encapsulated biological indicator is suitable as taught herein for use in that system. Others systems wherein the present indicator can be used will be known to those skilled in the art.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of assuring completeness of a decontamination process for eliminating microbial contamination, the method comprising:

encapsulating reference microorganisms in a hydrophilic microporous enclosure having pores that are smaller than the microorganisms such that the reference microorganisms are trapped therein, it being sufficiently porous to pass anti-microbial liquids therethrough;

immersing the microporous enclosure and items to be decontaminated in the anti-microbial liquid;

removing the enclosure from the anti-microbial liquid and immersing the enclosure in a culture medium;

determining whether any of the reference microorganisms grow in the culture medium.

2. The method as set forth in claim 1 wherein the antimicrobial liquid includes a strong oxidant, the reference microorganism enclosure being sufficiently resistant to antimicrobial liquid and strong oxidants so that the reference microorganisms are not released therefrom.

3. The method as set forth in claim 1 wherein the encapsulating step includes:

inoculating a carrier element with the reference microorganisms;

after inoculating the carrier element, wrapping the microorganism-inoculated element in the hydrophilic microporous membrane.

4. The method as set forth in claim 1 wherein the hydrophilic microporous enclosure is a microporous plastic tube with a hollow interior and wherein the encapsulating step includes loading the microorganisms into the hollow interior of the tube;

sealing ends of the tube.

5. The method as set forth in claim 4 wherein the microporous plastic tube is extruded and wherein the reference microorganisms are extruded into the hollow interior of the tube concurrently with the extruding of the microporous plastic tube.

6. The method as set forth in claim 4 wherein the microorganisms are mixed with a liquid prior to being loaded into the hollow interior of the microporous tube.

7. A method of assuring completeness of a decontamination process for eliminating microbial contamination, the method comprising:

encapsulating reference microorganisms in a hydrophilic microporous enclosure having pores that are smaller than the microorganisms such that the reference microorganisms are trapped therein, the hydrophilic microporous enclosure being sufficiently porous to pass antimicrobial liquids therethrough;

immersing the hydrophilic microporous enclosure and items to be decontaminated in a peracetic acid antimicrobial liquid;

removing the enclosure from the peracetic acid liquid and immersing the enclosure in a liquid culture medium;

determining whether any of the reference microorganisms grow in the culture medium.

\* \* \* \* \*